United States Patent [19]
Pritchard

[11] 3,990,438
[45] Nov. 9, 1976

[54] BONE FRACTURE FIXATION AND COMPRESSION APPARATUS

[76] Inventor: Rowland W. Pritchard, 205 French St., Bangor, Maine 04401

[22] Filed: Apr. 21, 1975

[21] Appl. No.: 569,782

[52] U.S. Cl. .......................................... 128/92 BC
[51] Int. Cl.² ........................................... A61F 5/04
[58] Field of Search ............ 128/92 R, 92 B, 92 BA, 128/92 BB, 92 BC, 83

[56] References Cited
UNITED STATES PATENTS

| | | | |
|---|---|---|---|
| 2,121,193 | 6/1938 | Hanicke | 128/92 BB |
| 2,243,717 | 5/1941 | Moreira | 128/92 BB |
| 2,821,979 | 2/1958 | Cameron | 128/92 BC |
| 3,051,169 | 8/1962 | Grath | 128/92 BB |
| 3,374,786 | 3/1968 | Callender, Jr. | 128/92 BB |
| 3,678,925 | 7/1972 | Fischer et al. | 128/92 BB |
| 3,760,802 | 9/1973 | Fischer et al. | 128/92 BC |

FOREIGN PATENTS OR APPLICATIONS

| | | | |
|---|---|---|---|
| 1,136,123 | 4/1902 | France | 128/92 BB |

Primary Examiner—John D. Yasko
Attorney, Agent, or Firm—Woodard, Weikart Emhardt & Naughton

[57] ABSTRACT

A lag screw member and a compression screw for maintaining a broken bone fragment fixed adjacent the principal bone and for applying compression force between the fragment and the principal bone. The lag screw member includes a first end with cutting threads for anchoring the lag screw member within the principal bone. The other end of the lag screw member includes a threaded socket for receiving the threaded portion of the compression screw after it passes through the bone fragment. The broad slotted head of the compression screw holds the bone fragment under pressure against the principal bone when the compression screw is rotated into the socket of the lag screw member.

5 Claims, 8 Drawing Figures

BONE FRACTURE FIXATION AND COMPRESSION APPARATUS

BACKGROUND OF THE INVENTION

1. Field of the Invention

The invention is in the field of medical apparatus for fixation and compression of a broken bone fragment relative to the principal bone.

2. Description of the Prior Art

In the prior art, several attempts have been made to anchor an intramedullary pin within the principal bone in the case of a bone fracture and to maintain the broken bone fragment adjacent the principal bone. Examples of such devices are shown in U.S. Pat. No. 3,763,855 to McAtee and U.S. Pat. No. 2,821,979 to Cameron. These devices require the insertion of a lateral element through the principal bone at a point distant from the location of the fracture.

The use of a surgical screw for bone fixation is shown in U.S. Pat. No. 2,612,159 to Collison. A different screw-type bone fixation device is shown in U.S. Pat. No. 3,779,239 to Fischer et al. Various other screw-type connectors for fractured bones with expanding-head connectors are shown in Fischer U.S. Pat. Nos. 3,678,925, 3,782,374, 3,716,051, and 3,805,775.

These prior art devices are generally more complicated than that disclosed in the present application, and often have the difficulty of not being capable of conformity to the bone contours without protrusions.

SUMMARY OF THE INVENTION

In the presently disclosed embodiment of the invention, two components are utilized, a lag component and a compression component. The lag component includes means for being embedded in the principal bone and has means for adjustably retaining the compression component when the compression component is inserted through the bone fragment adjacent the principal bone. There are no extra or protruding components to create problems after the fixation of the bone fragment.

One embodiment of the present invention comprises an apparatus for the fixation and compression of a broken bone fragment relative to the principal bone comprising a compression member having a shank portion for passing through the bone fragment and a broader head portion for engaging the bone fragment, and a lag member having a first end portion including means for embedding the first end portion in the principal bone and a second end portion including means for engaging the first portion of the compression member and for varying the distance between the head portion of the compression member and the lag member.

It is an object of the present invention to provide a two piece bone fixation and compression apparatus for the setting of fractures.

It is a further object of the present invention to provide such an apparatus in which there is a compression member and a lag member, the lag member including means for embedding the lag member in bone and means for adjustably retaining the compression member.

Further objects and advantages of the present invention shall be apparent from the following detailed description and accompanying figures.

DESCRIPTION OF THE PREFERRED EMBODIMENT

Figure 1:
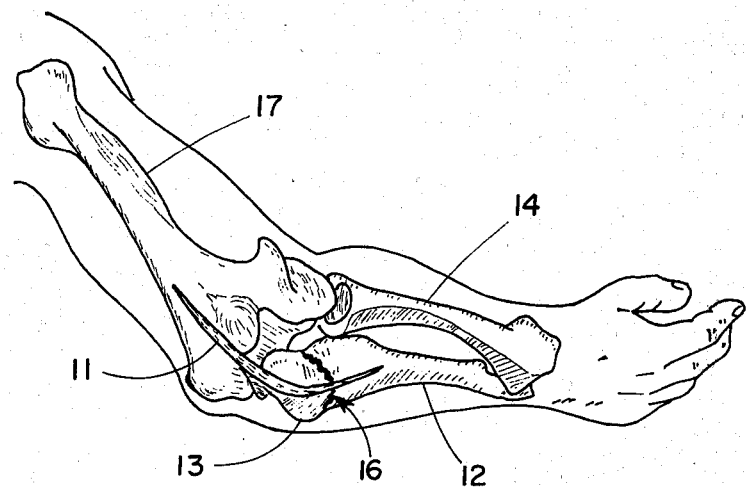
FIG. 1 is a diagrammatic representation of an ulnar fracture.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 1, there is shown diagrammatically an operative incision 11 in the vicinity of the olecranon process of the ulna 12. Also shown are radius 14 and humerus 17. A bone fragment 13 in the vicinity of the olecranon process is broken away from ulna 12 along a fracture line indicated at 16.

Figure 2:
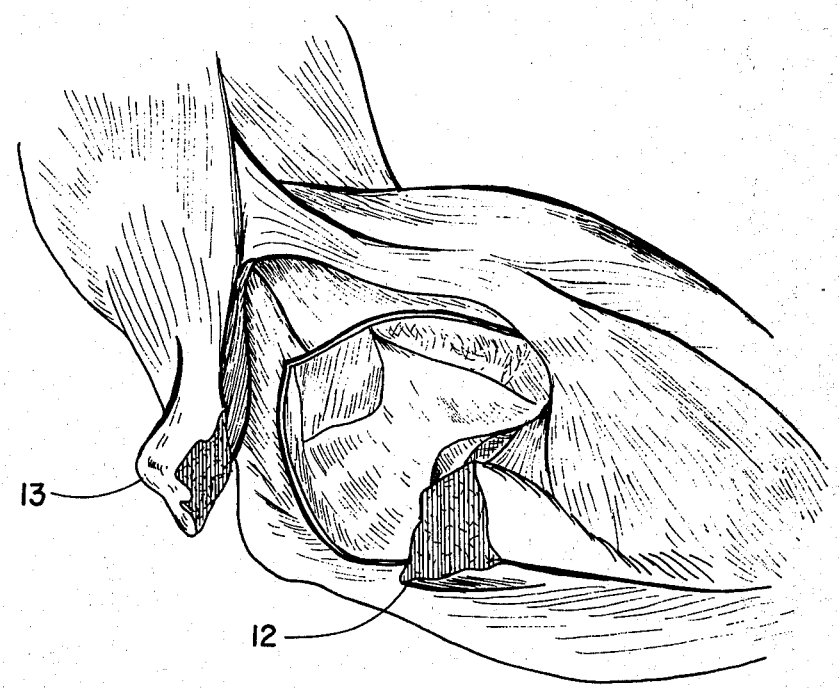
FIG. 2 is an enlarged view of a portion of FIG. 1 showing the bone and muscle tissue in the vicinity of the fracture.
Figure 3:
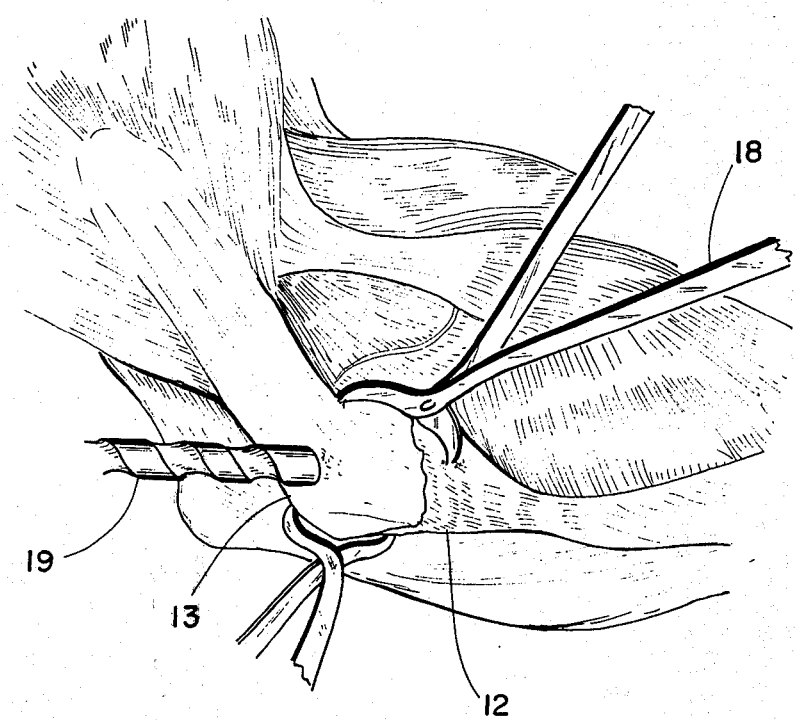
FIG. 3 shows the arm portion of FIG. 2 with the fractured ulna held in place for drilling.

FIG. 2 is a view of the fracture exposed together with a portion of the elbow joint and its associated tendons and muscles. Fragment 13 is shown separated from ulna 12. In FIG. 3, fragment 13 is held in position adjacent ulna 12 using forceps 18 and a drill (not shown) drives quarter inch drill bit 19 to drill proximal fragment 13 for subsequent insertion of the lag screw component of the fixation and compression apparatus.

Figure 4:
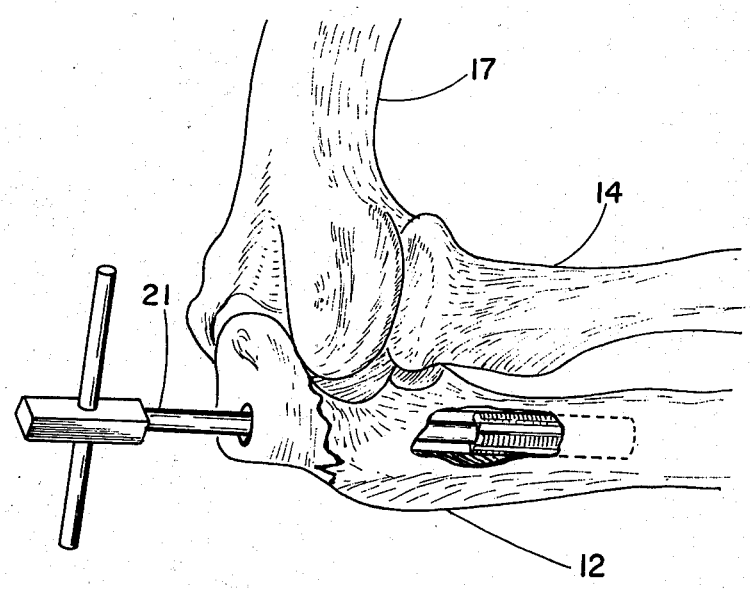
FIG. 4 shows the intramedullary tapping of the ulna.
Figure 5:
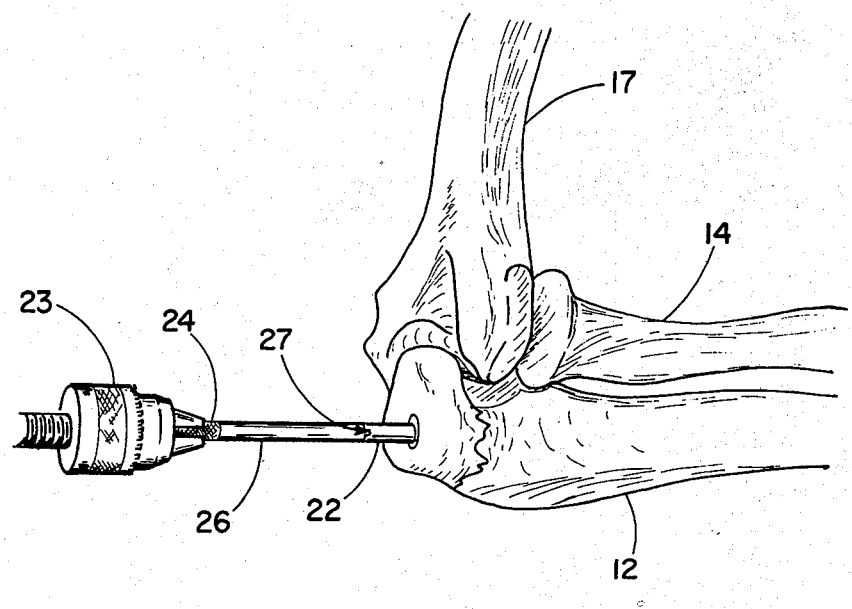
FIG. 5 shows the insertion of the lag member according to an embodiment of the present invention.

FIG. 4 shows the medullary canal being tapped to the greatest length possible by tap 21. The appropriate length lag screw to be used may be read from calibrations on tap 21. The depth of the tapping is generally about ½ inch further than the length of the lag screw selected. As shown in FIG. 5, lag screw 22 is inserted into the tapped medullary canal of ulna 12. A drill (not shown) coupled through chuck 23 drives a lag screw insertion device comprising outer housing 26 and interior member 24. Member 24 is gripped by the chuck and has at its other end a threaded portion received within the head of lag screw 22. Housing 26 is held in engagement with lag screw 22 and has a pair of raised portions 27 for engaging slots in the head of lag screw 22.

Figure 8:
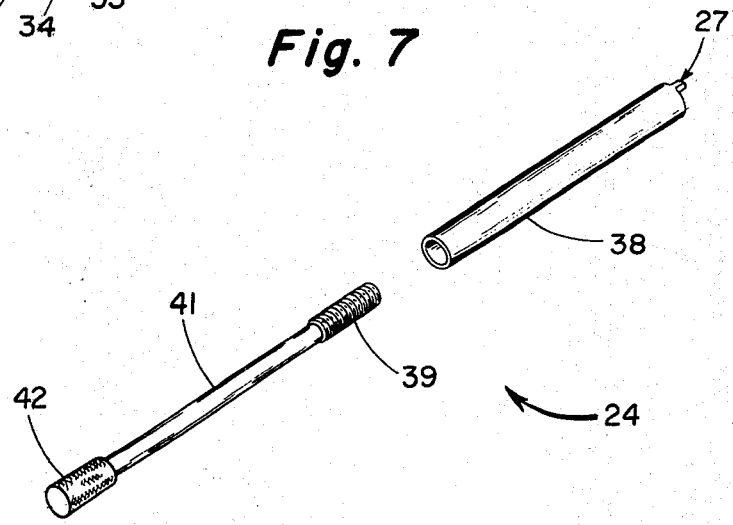
FIG. 8 shows the insertion tool utilized in FIG. 5.

The insertion device 24 is shown in greater detail in FIG. 8. Head portion 42 is received within the chuck and is connected to an extended shaft 41 which terminates in a threaded portion 39. This threaded portion 39 is received within the head of lag screw 22. Outer tube 38, as shown, includes the projections 27 described above for engaging the slots of lag screw 22.

Figure 6:
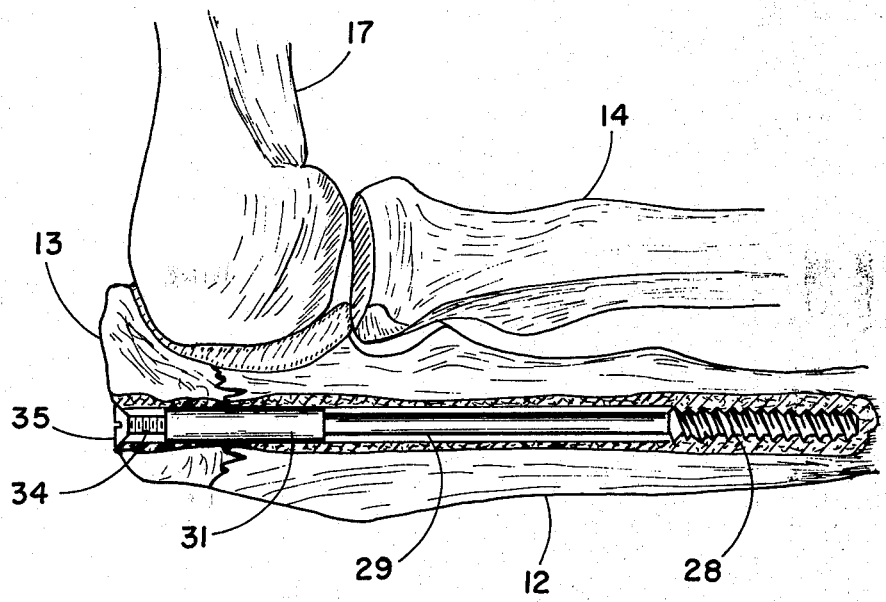
FIG. 6 shows the emplaced fracture fixation and compression apparatus according to the present invention.
Figure 7:
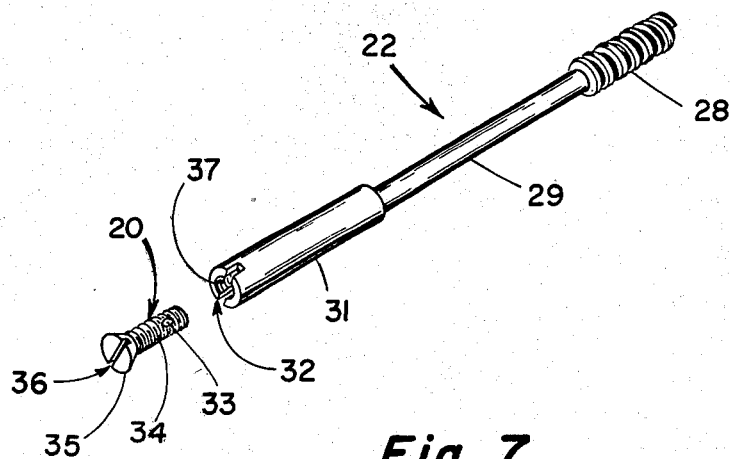
FIG. 7 shows the compression and lag members of the presently disclosed fracture fixation and compression apparatus.

Referring now to FIGS. 6 and 7, the fracture fixation and compression apparatus according to the present invention is shown in detail. In FIG. 6, the apparatus is shown in its final implanted position, and FIG. 7 is an exploded view of the apparatus. The fixation and compression apparatus includes a lag screw 22 and a compression screw 20. The lag screw member 22 includes a threaded end portion 28 with threads to grip the tapped intramedullary canal of the ulna. Lag screw member 22 further includes a body portion 29 and an enlarged head 31 which includes a channel or socket therein for receiving compression screw 20. The interior of head 31 is threaded as shown at 37 for receiving compression screw 20 in threaded engagement and further includes a pair of slots 32 to facilitate insertion of lag screw member 22.

Compression screw 20 is a flat head screw having a head portion 35 and a threaded shank 34. After the lag screw is inserted into the intramedullary canal of the ulna as shown in FIG. 5, the compression screw 20 is introduced through the hole drilled in the olecranon fragment and threaded into head 31 of lag screw member 22. The head 35 of compression screw 20 engages the fragment 13, and as screw 20 is inserted into further threaded engagement with lag screw 22, fragment 13 is pressed against and fixed in position relative to ulna 12. Compression screw 20 includes a slot 36 for receiving a screw driver blade to effect the threaded engagement between screw 20 and head 31 of the lag screw 22, and compression screw 20 also includes a nylon thread lock dot 33 to inhibit the loosening of screw 20 within the channel in head 31 after assembly.

The lag screw member 22 is provided in a plurality of lengths, such as in quarter inch increments from 2 and ½ inches to 5 inches. The compression screw 20 is ½ inch long, with a flat head and nylon thread lock as described above. As can be seen from FIG. 6, the flat head configuration of screw 20 permits the screw to be inserted to a location that it does not protrude from the olecranon fragment 13 after assembly. The apparatus as shown provides a strong, firm and rigid fixation of the ulnar fracture and active motion of the joint is permissible within 5 to 6 days. This is in contrast to the typical 6 to 8 week emplacement of an above-the-elbow cast using the prior art devices provided for fixation of ulnar fractures.

While there have been described above the principles of this invention in connection with specific apparatus, it is to be clearly understood that this description is made only by way of example and not as a limitation in the scope of the invention.

What is claimed is:

1. Apparatus for the fixation and compression of a broken elbow bone fragment relative to the ulna of the human arm consisting of:
   a. an elongated lag member having,
      1. a proximal end portion positionable near the bone fragment including an axially aligned threaded aperture therein and means for permitting the lag member to be threadedly inserted into the ulna,
      2. a cutting thread distal end portion adaptable to be threadedly received within the medullary canal of the ulna, and
      3. an intermediate portion connecting said proximal end portion and said distal end portion, the intermediate portion being thinner than the proximal end portion and the proximal end portion being positionable to be in contact with the interior of both the bone fragment and the ulna; and
   b. a compression screw having,
      1. a threaded shank portion threadedly received within the threaded aperture in the proximal end portion of the lag member, and
      2. a broader head portion, adaptable to engage the elbow bone fragment, the head portion of the compression member including an indentation to receive a tool to drive the compression member into threaded engagement within the proximal end portion of the lag member.

2. The apparatus of claim 1 in which the proximal end of the lag member is slotted.

3. The apparatus of claim 1 in which the threaded portion of the compression member includes a flexible locking dot within its threads.

4. The apparatus of claim 1 in which the compression screw is a flat head screw.

5. A method for the fixation and compression of a broken elbow bone fragment relative to the ulna comprising the steps of:
forming a channel through the bone fragment;
tapping the intramedullary canal of the ulna;
selecting a lag member whose length is dependent upon the extent of tapping of the intramedullary canal;
inserting the partially threaded lag member, having a socket at its proximal end which is internally threaded and larger than the intermediate portion of the member operable to adjustably engage the shank of a compression member, into threaded engagement within the tapped intramedullary canal;
inserting the shank of a compression member through the channel in the fragment into engagement with the socket of the lag member, a head on the compression member engaging the bone fragment; and
increasing the engagement of the shank of the compression member within the socket of the lag member to obtain desired compression and fixation of the fragment relative to the ulna, the head of the compression member being received essentially within the bone fragment and the enlarged proximal end portion of the lag member being positioned to span the fracture site.

* * * * *